United States Patent [19]

Hirano et al.

[11] Patent Number: 5,401,742
[45] Date of Patent: Mar. 28, 1995

[54] POLYMERIC CONJUGATE OF METHOTREXATE COMPOUND AND PYRAN COPOLYMER AND METHOD FOR THE PREPARATION THEREOF

[75] Inventors: Takashi Hirano; Takeshi Todoroki; Shinichi Ohashi; Tomokuni Kokubu; Hideaki Tanaka, all of Ibaraki, Japan

[73] Assignee: Japan, as represented by Director General of Agency of Industrial Science and Technology, Tokyo, Japan

[21] Appl. No.: 214,467

[22] Filed: Mar. 18, 1994

[30] Foreign Application Priority Data

May 11, 1993 [JP] Japan ................... 5-132873

[51] Int. Cl.⁶ .............. A61K 31/505; C08L 33/06; C08F 281/00
[52] U.S. Cl. ............... 514/249; 525/327.2; 525/375
[58] Field of Search ............ 514/249; 525/327.2, 525/375

[56] References Cited

U.S. PATENT DOCUMENTS

4,182,800 1/1980 Ringsdorf et al. ............ 525/375
4,520,162 5/1985 Hirano et al. ............... 525/375

*Primary Examiner*—Joseph E. Evans
*Attorney, Agent, or Firm*—Wenderoth, Lind & Ponack

[57] ABSTRACT

Methotrexate, which is a known anticancer agent, can be converted into a polymeric conjugate with a pyran copolymer, which in itself has a certain anticancer effect, by a method in which an alkylene diamine is reacted with the carboxyl group of the methotrexate molecule to give an amidation product having a free amino group in a molecule, which is then reacted with the carboxyl group of the pyran copolymer, of which at least 10% of the repeating units have been modified with the methotrexate residue. The polymeric conjugate has sustained releasability of the methotrexate compound in blood serum so that an excellent therapeutic effect can be obtained by the administration thereof against cancers with little problems due to the side effects caused by an unduly high concentration of the drug in blood unavoidable when methotrexate as such is administrated.

3 Claims, 2 Drawing Sheets

POLYMERIC CONJUGATE OF METHOTREXATE COMPOUND AND PYRAN COPOLYMER AND METHOD FOR THE PREPARATION THEREOF

BACKGROUND OF THE INVENTION

The present invention relates to a novel polymeric conjugate of a methotrexate derivative and a pyran copolymer exhibiting an excellent anticancer effect and a method for the preparation thereof.

Methotrexate is a known anticancer agent with wide therapeutic applications exhibiting remarkable effectiveness against acute lymphocytic leukemia, mammary cancer, lung cancer, head and neck cancer and the like. It is an antagonist of folic acid and has an activity to kill cells by the inhibition of DNA synthesis when it is strongly bound with the dihydrofolate reductase.

Along with the excellent anticancer activity, however, methotrexate exhibits serious side effects such as gastrointestinal tract disorder, decrease of leukocytes and blood platelets, renal disfunction and the like due to the toxicity against normal cells at a growing stage. Therefore, it is necessary that methotrexate must be clinically administered avoiding the possible side effects.

When a cancer patient is administered with a low-molecular anticancer agent such as methotrexate, in general, the concentration thereof in blood is rapidly decreased with a relatively short half life time. While the anticancer activity of methotrexate is a consequence of the activity thereof to the S phase in the cell cycle of cancer cells, 36 to 48 hours, the anticancer effect obtained by methotrexate is limited. Although the concentration of the agent in blood can be sustainedly increased to be effective on cancer cells by increasing the dose, this way cannot be undertaken for methotrexate because the concentration thereof in blood may be unduly high within a period so as to cause damages on normal cells such as mucosa cells at the growing phase.

It is a natural idea that the anticancer effectiveness of an anticancer agent such as methotrexate can be enhanced without increasing the toxicity when the anticancer agent is sustainedly released into the blood by some means so that the concentration thereof in blood could be maintained in such a level as to exhibit the desired anticancer effect with minimum side effects. Known methods for sustainedly releasing a drug into the patient's blood include the direct method such as the continuous infusion clinically undertaken heretofore and the indirect method in which the anticancer agent is administrated as incorporated into liposomes or polymeric microspheric particles to avoid the damage on the patient's body. The latter method is highlighted as an excellent method for the administration of a drug with strong side effects because the concentration thereof in blood can be effectively controlled by a single administration. The so-called "drug delivery system" (DDS) including these methods or concepts is under rapid progress in recent years in the field of medical and pharmaceutical science. The basic principle of DDS is to give a necessary drug to the appropriate position of the body, at an appropriate time and in an appropriate concentration. Utilization of a conjugate of a drug and a polymeric compound as a carrier is also a promising method of DDS in respect of the long half life time of the polymeric compound in the body and the sustained releasability of the drug from the polymer conjugate.

This means of sustained release of a drug by forming a polymer conjugate would be particularly effective for a drug such as methotrexate of which enhancement of the anticancer effect and decrease of the side effects can be expected by controlling the concentration thereof in blood at an appropriate level.

Various proposals and attempts have been made heretofore for methotrexate from this standpoint of conjugate formation. For example, a conjugate thereof with serum albumin was reported recently in Neoplasma, volume 37, pages 343-349 (1990). Since albumin is a protein derived from a living body consisting of a large number of amino acid residues, there is no information on the type and sites of the chemical bond between albumin and methotrexate. As a consequence, the anticancer activity of such an albumin conjugate of methotrexate is almost identical against B16 melanoma with that of methotrexate as such. In short, no polymeric conjugate known heretofore can exhibit a superior anticancer activity to that of methotrexate per se.

Despite the so great possibility of enhancement of the anticancer effect to be obtained by the sustained drug relesability with a conjugate of methotrexate and a polymer as is expected from the pharmacological mechanism, no effective means is reported heretofore by which a conjugate of methotrexate with a polymer can exhibit higher anticancer activity than that of methotrexate as such. One of the reasons therefor is the absence of precise information or knowledge which enables definitively designing the bonding type between the molecules of the polymer and methotrexate to meet the particular requirements. It would be an idea therefore that the glutamic acid residue at the end of the methotrexate is utilized for bonding with a polymer molecule so that the desired sustained releasability of the drug could be established by selecting the type of the polymer to obtain higher anticancer activity than methotrexate as such.

SUMMARY OF THE INVENTION

The present invention accordingly has an object to provide a polymer conjugate of methotrexate which ensures sustained releasability of methotrexate in a living body by administration to exhibit excellent anticancer activity with minimum side effects. The polymeric compound which can be the polymeric constituent of the inventive polymer conjugate with methotrexate is a so-called pyran copolymer capable of forming a bond with methotrexate after modification of the glutamic acid residue at the molecular end.

Thus, the polymeric conjugate of methotrexate of the invention is a methotrexate conjugate of a pyran copolymer which consists of: from 10 to 500 in number of the repeating units represented by the general formula in which at least 10% by moles of the groups denoted by R are each a modified methotrexate residue expressed by the formula (II)

or (III)

in which the subscript n is a positive integer not exceeding 12, the remainder of the groups denoted by R, if any, being hydroxyl groups, in the form of a free acid or in the form of a salt thereof.

The above defined methotrexate-pyran copolymer conjugate of the invention in the form of a free acid can be prepared by the method which comprises the step of: reacting, in the presence of a water-soluble organic solvent, a pyran copolymer represented by the general formula

(IV)

in which the subscript m is a positive integer in the range from 10 to 500, with a methotrexate compound represented by the general formula (V)

or (VI)

in which the subscript n is a positive integer not exceeding 12 in an amount of at least 10% by moles relative to the repeating units in the pyran copolymer represented by the above given formula (IV).

DETAILED DESCRIPTION OF THE PREFERRED EMBODIMENTS

As is described above, the polymeric moiety in the polymer conjugate of methotrexate of the invention is a so-called pyran copolymer which is in itself known to have anticancer activity by activating the immunological system as a defensive function of living organisms as is reported in Pure and Applied Chemistry, volume 46, pages 103-113 (1976). It is expected that, when a conjugate is formed by bonding a high-molecular pyran copolymer and a low-molecular anticancer agent, the low-molecular anticancer agent would be sustainedly released in a living body when a patient is administrated with the polymeric conjugate so that the concentration of the anticancer agent in blood could be maintained sustainedly at an appropriate level by virtue of the good residential behavior of the polymer as a carrier thereof. In addition, another possibility can be expected for a synergistic anticancer effect because of the different anticancer mechanisms between the immunological activation of the pyran copolymer and the cytocidal effect of the low-molecular anticancer agent. Since the molecule of a pyran copolymer has a large number of the ring units of acid anhydride having high chemical reactivity, pyran copolymers can readily react with various functional groups in the drug molecule such as hydroxy and amino groups to give a polymeric conjugate of a high drug content.

Furthermore, the thus produced polymeric conjugate is usually highly water-soluble by virtue of the so many number of free carboxyl groups formed by the bond cleavage of the acid anhydride rings as well as the hydrophilic pyran rings forming the main chain of the polymer molecules. When a pyran copolymer and a low-molecular drug molecule are bonded by forming an amide linkage or an ester linkage, even the less hydrolyzable amide linkage can be cleaved to release the drug even without participation of a hydrolase as a result of the hydrolysis taking place by the back-attack of the carboxyl group bonded to the pyran ring at the adjacent position to the amide or ester linkage. The superior performance of a pyran copolymer as a polymeric carrier of methotrexate could be explained by the above described characteristics including the synergistic enhancement of the anticancer effect, high content of the drug in the polymeric conjugate, high water-solubility, hydrolyzability of the bond by the influence of the intramolecular functional group and so on.

The pyran copolymer as the polymeric base of the inventive polymer conjugate of methotrexate is represented by the above given formula (IV) and can be prepared from divinyl ether and maleic anhydride according to the synthetic procedure described in Macromol. Synthesis, volume 8, pages 89–94 (1982). Pyran copolymers in themselves have anticancer activity so that synergistic enhancement of the anticancer activity can be expected when a pyran copolymer is combined with a low-molecular anticancer agent to form a conjugate. The pyran copolymer as the polymer base of the inventive conjugate should have an average molecular weight in the range from about 3000 to about 100,000 corresponding to the value of the subscript m in the formula (IV) of 10 to 500. When the average molecular weight of the pyran copolymer is too high, a problem is caused in the excretory behavior thereof from the living body while, when the average molecular weight thereof is too low, the residential time of the drug after administration would be unduly decreased.

As a type of the conjugate-forming reaction between a pyran copolymer and methotrexate, a direct reaction is reported in Makromol. Chem., volume 179, pages 1719–1843 (1978) between the amino group of the aromatic pteridine ring in the methotrexate molecule and the acid anhydride ring in the pyran copolymer. The conjugate-forming linkage of this type, however, is quite unstable and the methotrexate molecules bonded to the pyran copolymer molecules in this way are completely released within only a few minutes when the conjugate is administered to a living body. Accordingly, the anticancer activity of such a conjugate is not higher than that of methotrexate per se in the administration test using L1210 leukemic mice as is reported in Cancer Treat. Rep., volume 62, pages 1837–1843 (1978). In conducting extensive investigations with an object to obtain a polymeric conjugate of methotrexate with a pyran copolymer having adequate stability, the inventors have come to an idea that it would be a promising way to prepare a polymeric conjugate by forming a linkage between a pyran copolymer and methotrexate by the reaction of the carboxyl groups in the acid anhydride structure of the pyran copolymer with a methotrexate compound derived from methotrexate by introducing an amino group-terminated linking unit into the carboxyl group in the glutamic acid residue of the methotrexate molecule.

Namely, the very scope of the present invention consists in the preparation of a polymeric conjugate of methotrexate with a pyran copolymer by the reaction of a methotrexate derivative having a reactive amino group obtained by the reaction of an alkylene diamine with the carboxyl group at the glutamic acid residue of the methotrexate. To explain in more detail, a solution of the methotrexate derivative in an alkaline buffer solution and a pyran copolymer are reacted in an organic solvent having miscibility with water followed by ultrafiltration and the reaction product is precipitated in a large volume of acetone or methanol followed by drying or direct freeze-drying of the reaction mixture to give a polymeric conjugate. If desired, the polymeric conjugate thus obtained in the form of a free acid can readily be converted into a salt with a metallic ion of sodium, potassium, calcium, magnesium and the like having pharmacological compatibility.

The content of the methotrexate moiety in the thus obtained polymeric conjugate is preferably in the range from 5 to 67% by weight. The content of 5% by weight corresponds to a conjugate in which 10% by moles of the groups denoted by R in the general formula (I) are substituted by the methotrexate groups of the formula (II) or (III) while the content of 67% corresponds to a conjugate in which all of the groups denoted by R in the general formula (I) are substituted by the methotrexate groups. These percentages of substitution by the methotrexate groups is referred to as the degree of MTX substituion hereinbelow.

As to the sustained-releasability of methotrexate from the polymeric conjugate with a pyran copolymer, an in vitro test using human serum at 37° C. indicated that 30% of the methotrexate groups were released within 72 hours from a conjugate with a pyran copolymer having a value of $m=110$ in the formula (IV) corresponding to an average molecular weight of 30,000, in which 29% of the groups R in the general formula (I) were substituted by the methotrexate groups of the formula (III) with $n=6$.

Evaluation of the anticancer activity of the polymeric conjugate was undertaken for the same polymeric conjugate as above in an animal test using P388 leukemic mice as the test animals. Thus, each of six a group of $CDF_1$ female mice of 6 weeks age after 24 hours from inoculation of $1 \times 10^6$ P388 leukemia cells in the abdominal cavity was administered in the abdominal cavity with the drug and a comparison was made for the survival time between the test groups and the control group. Namely, the increase in the life time relative to the control group was calculated from the median of the survival days in each test group to give a criterion of evaluation. The results were that, while the life prolongation in the group by the administration of methotrexate per se was 54%, the value for the test group by the administration of the polymeric conjugate was 163%. This difference is significant in favor of the polymeric conjugate even by the Mann-Whitney U-test ($\alpha<0.05$) established as a biologically statistic method.

A support is given for the therapeutic valuableness of the methotrexate conjugate with a pyran copolymer by the above described results of the in vitro and in vivo tests showing that the methotrexate compound having anticancer activity is sustainedly released in human serum from the polymeric conjugate to exhibit a synergistic therapeutic effect with the pyran copolymer having anticancer activity in itself.

In the following, the present invention is described in more detail by way of examples.

EXAMPLE 1

A solution of 1.6 g of methotrexate and 4.0 g of 1,6-diaminohexane dissolved in 40 ml of N,N-dimethylformamide with admixture of 0.8 g of a water-soluble carbodiimide was agitated for 2 hours at room temperature by using a magnetic stirrer to effect the amidation reaction and the reaction mixture was added dropwise into 1 liter of acetone to precipitate the reaction product which was collected by filtration and dried to give 2.2 g of a product powder. This product was subjected to a purification and fractionation treatment by the method of preparative high performance column chromatography using a chromatographic column of 20 mm diameter and 25 cm length with a 0.2M ammonium acetate buffer solution of pH 4.6 with admixture of each 10% by volume of acetonitrile and methanol as an eluent to give 0.4 g and 0.5 g of the 1,6-diaminohexane derivatives of the formula (V)

a PM 30 membrane (a product by Amicon Co.) with a fractionation molecular weight of 30,000, followed by washing with distilled water to remove the unreacted methotrexate derivative and the borate. The solution remaining on the membrane was, after measurement of the ultraviolet absorption at a wavelength of 313 nm to confirm absence of the unreacted methotrexate derivative, subjected to sterilization by passing through a sterilizing filtration membrane of 0.1 μm pore diameter (a product by Millipore Co.) followed by freeze-drying to give 52 mg of a fleecy yellow solid. The experimental result was substantially the same as above when the methotrexate derivative of the formula (V) (n=6) was replaced with that of the formula (VI) (n=6) or acetone as the reaction solvent was replaced with dimethylsulfoxide or N-methylpyrrolidone.

Figure 1:
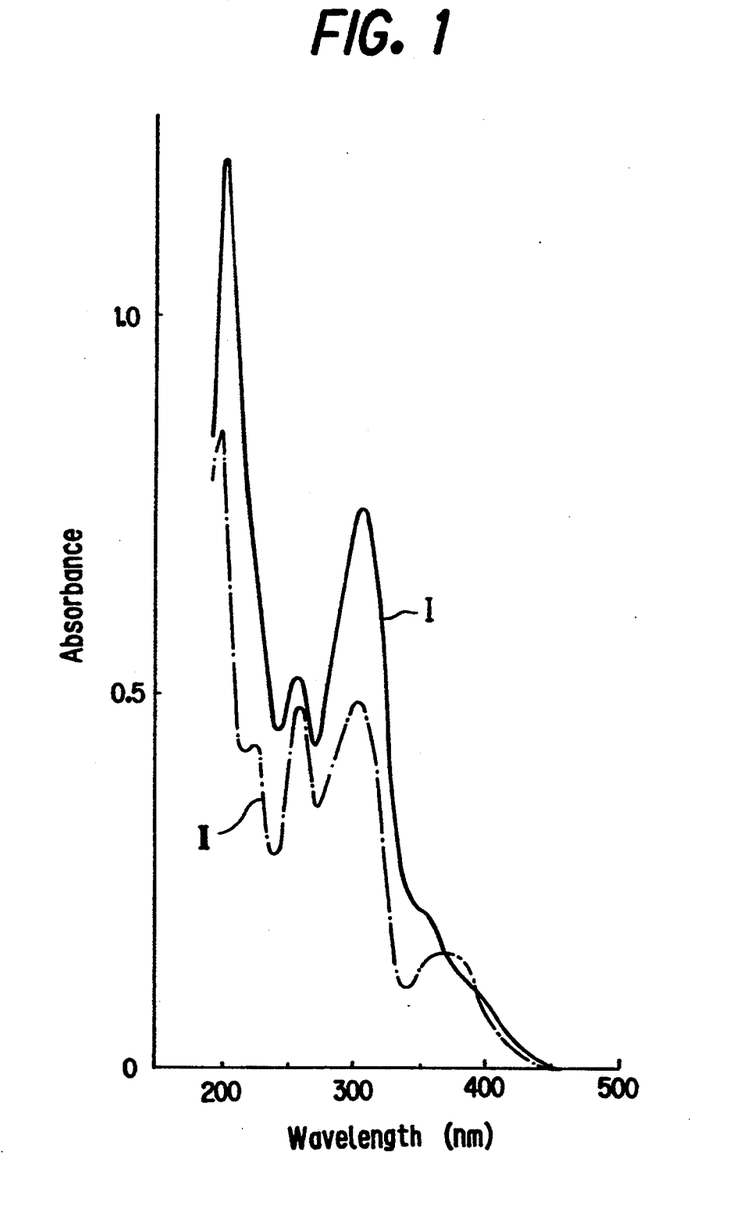
FIG. 1 is an ultraviolet absorption spectrum of the polymeric conjugate prepared in Example 1 in an aqueous solution.

Different from methotrexate per se which is hardly soluble in neutral water, thus obtained polymeric conjugates of methotrexate with a pyran copolymer each have an extremely high solubility in neutral water and physiological saline solution. FIG. 1 shows the ultraviolet absorption spectrum of an aqueous solution of the polymeric conjugate in a concentration of 50 mg/liter (curve I) and the spectrum of methotrexate per se in a concentration of 3.9 mg/liter (curve II) with the absorbance for an optical path length of 1 cm as the ordinate.

and (VI)

in which the subscript n was 6, respectively. The former derivative isolated in the form of an acetate was subjected to elemental analysis to give analytical values of: C 54.74%; H 6.36%; and N 22.48% in good coincidence with the theoretical values of: C 54.89%; H 6.58%; and N 22.86% calculated for the molecular formula $C_{28}H_{40}N_{10}O_6$. The results of synthetic experiment were substantially the same as above when N,N-dimethylformamide was replaced with the same volume of dimethylsulfoxide or N-methylpyrrolidone.

The methotrexate derivative of the formula (V) prepared above in an amount of 25 mg was dissolved in 15 ml of a 0.2M borate buffer solution of pH 8.6 and the solution was admixed with a solution of 20 mg of a pyran copolymer having an average molecular weight of 30,000 corresponding to 110 of the value of the subscript m in the formula (IV) in 2 ml of acetone to give a reaction mixture. After adjustment of the pH to 8.6 using a 0.2M aqueous solution of sodium hydroxide, the reaction mixture was agitated for 2 hours at room temperature by using a magnetic stirrer to effect the amidation reaction of the pyran copolymer. The reaction mixture was subjected to ultramembrane filtration using As is clear from this figure, the ultraviolet absorption spectra are substantially identical between the polymeric conjugate and methotrexate per se at least relative to the wavelengths of characteristic peaks and relative intensities thereof. The intensity of ultraviolet absorption at a wavelength of 309 nm could be utilized for the quantitative determination of the methotrexate moiety in the conjugate. The methotrexate content in the conjugate prepared in this example was 41% by weight corresponding to a degree of MTX substitution of 33% assuming a value of 6 for the subscript n in the formula (II) or (III).

EXAMPLE 2

An aqueous solution of 20 mg of the polymeric conjugate prepared in Example 1 in 10 ml of distilled water was admixed with a 0.1M aqueous solution of sodium hydrogen carbonate so as to have a pH of 7.8. The aqueous solution was washed over an ultrafiltration membrane (PM 30, supra) and subjected to sterilization in the same manner as in Example 1 followed by freeze-drying to give 21 mg of a fleecy yellow solid which was a sodium salt of the polymeric conjugate. This polymeric conjugate of methotrexate in the form of a sodium salt had a solubility in water or physiological saline solution still higher than the polymeric conjugate in the free acid form. The ultraviolet absorption spectrum of an aqueous solution of this sodium salt of the polymeric conjugate was substantially identical with that of the free acid polymeric conjugate. The methotrexate content therein was 35% by weight calculated from the ultraviolet absorption of an aqueous solution thereof.

EXAMPLE 3

The methotrexate derivative of the formula (V) (n=6) prepared in Example 1 in an amount of 68 mg was dissolved in 15 ml of a 0.2M borate buffer solution of pH 8.6 and the solution was admixed with a solution of 68 mg of a pyran copolymer having an average molecular weight of 5,000 corresponding to 18 of the value of the subscript m in the formula (IV) in 2 ml of acetone to give a reaction mixture. After adjustment of the pH to 8.6 using a 0.2M aqueous solution of sodium hydroxide, the reaction mixture was agitated for 2 hours at room temperature by using a magnetic stirrer to effect the amidation reaction of the pyran copolymer. The reaction mixture was subjected to membrane filtration using a PM 10 membrane (a product by Amicon Co.) with a fractionation molecular weight of 10,000 followed by washing with distilled water to remove the unreacted methotrexate derivative and the borate. The solution remaining on the membrane was, after measurement of the ultraviolet absorption at a wavelength of 313 nm to confirm absence of the unreacted methotrexate derivative, subjected to sterilization by passing through a sterilizing filtration membrane of 0.1 $\mu$m pore diameter (a product by Millipore Co.) followed by freeze-drying to give 142 mg of a fleecy yellow solid. The experimental result was substantially the same as above when the methotrexate derivative of the formula (V) was replaced with that of the formula (VI) or acetone as the reaction solvent was replaced with dimethylsulfoxide or N-methylpyrrolidone.

The solubility behavior of the polymeric conjugate and the ultraviolet absorption spectrum of an aqueous solution thereof were substantially identical with those of the polymeric conjugate prepared in Example 1. The intensity of ultraviolet absorption at a wavelength of 309 nm could be utilized for the quantitative determination of the methotrexate moiety in the conjugate. The methotrexate content of the conjugate prepared in this example was 29% by weight corresponding to a degree of MTX substitution of 20% assuming a value of 6 for the subscript n in the formula (II) or (III).

EXAMPLE 4

The experimental procedure was substantially the same as in Example 3 excepting replacement of the pyran copolymer having an average molecular weight of 5,000 with the same amount of another pyran copolymer having an average molecular weight of 120,000 corresponding to 441 of the value of the subscript m in the formula (IV) and use of an ultrafiltration membrane PM 30 (see Example 1) in place of PM 10 in Example 3 to obtain 145 mg of a polymeric conjugate.

The solubility behavior of the polymeric conjugate and the ultraviolet absorption spectrum of an aqueous solution thereof were substantially identical with those of the polymeric conjugate prepared in Example 1. The intensity of ultraviolet absorption at a wavelength of 309 nm could be utilized for the quantitative determination of the methotrexate moiety in the conjugate. The methotrexate content of the conjugate prepared in this example was 29% by weight corresponding to a degree of MTX substitution of 20% assuming a value of 6 for the subscript n in the formula (II) or (III).

EXAMPLE 5

A solution of 454 mg of methotrexate and 840 $\mu$l of 1,3-diaminopropane dissolved in 40 ml of N,N-dimethylformamide with admixture of 230 mg of a water-soluble carbodiimide was agitated for 2 hours at room temperature by using a magnetic stirrer to effect the amidation reaction and the reaction mixture was added dropwise into 1 liter of acetone to precipitate the reaction product which was collected by filtration and dried to give 500 mg of a product powder. This product was subjected to a purification and fractionation treatment by the method of preparative high performance column chromatography in the same manner as in Example 1 to give 105 mg and 120 mg of the amidation products of methotrexate expressed by the formulas (V) and (VI), respectively, with the subscript n of 3. The former derivative isolated in the form of an acetate was subjected to elementary analysis to give analytical values of: C 52.00%; H 6.18%; and N 23.80% in good coincidence with the theoretical values of: C 52.62%; H 6.01%; and N 24.55% calculated for the molecular formula $C_{25}H_{34}N_{10}O_6$. The results of synthetic experiment were substantially the same as above when N,N-dimethylformamide was replaced with the same volume of dimethylsulfoxide or N-methylpyrrolidone.

The methotrexate derivative of the formula (V) (n=3) prepared above in an amount of 68 mg was dissolved in 15 ml of a 0.2M borate buffer solution of pH 8.6 and the solution was admixed with a solution of 68 mg of a pyran copolymer having an average molecular weight of 30,000 corresponding to 110 of the value of the subscript m in the formula (IV) in 2 ml of acetone to give a reaction mixture. After adjustment of the pH to 8.6 using a 0.2M aqueous solution of sodium hydroxide, the reaction mixture was agitated for 2 hours at room temperature by using a magnetic stirrer to effect the amidation reaction of the pyran copolymer. The reaction mixture was subjected to a purification treatment in the same manner as in Example 1 to give 129 mg of a fleecy yellow solid. The experimental result was substantially the same as above when the methotrexate derivative of the formula (V) was replaced with that of the formula (VI) (n=3) or acetone as the reaction solvent was replaced with dimethylsulfoxide or N-methylpyrrolidone.

The solubility behavior of the polymeric conjugate and ultraviolet absorption spectrum of an aqueous solution thereof were substantially identical with that in Example 1. The content of methotrexate in the polymeric conjugate was 33% by weight corresponding to the degree of MTX substitution of 25%.

EXAMPLE 6

A solution of 454 mg of methotrexate and 2.0 g of 1,12-diaminododecane dissolved in 40 ml of N,N-dimethylformamide with admixture of 422 mg of a water-soluble carbodiimide was agitated for 2 hours at room temperature by using a magnetic stirrer to effect the amidation reaction and the reaction mixture was added dropwise into 1 liter of acetone to precipitate the reaction product which was collected by filtration and dried to give 624 mg of a product powder. This product was subjected to a purification and fractionation treatment by the method of preparative high performance column chromatography in the same manner as in Example 1 to give 128 mg and 225 mg of the amidation products of methotrexate expressed by the formulas (V) and (VI), respectively, with the subscript n of 12. The former derivative isolated in the form of an acetate was subjected to elementary analysis to give analytical values of: C 58.87%; H 6.96%; and N 20.10% in good coincidence with the theoretical values of: C 58.60%; H 7.52%; and N 20.10% calculated for the molecular formula $C_{34}H_{52}N_{10}O_6$. The results of synthetic experiment were substantially the same as above when N,N-dimethylformamide was replaced with the same volume of dimethylsulfoxide or N-methylpyrrolidone.

The methotrexate derivative of the formula (V) (n=12) prepared above in an amount of 54 mg was dissolved in 15 ml of a 0.2M borate buffer solution of pH 8.6 and the solution was admixed with a solution of 54 mg of a pyran copolymer having an average molecular weight of 30,000 corresponding to 110 of the value of the subscript m in the formula (IV) in 2 ml of acetone to give a reaction mixture. After adjustment of the pH to 8.6 using a 0.2M aqueous solution of sodium hydroxide, the reaction mixture was agitated for 2 hours at room temperature by using a magnetic stirrer to effect the amidation reaction of the pyran copolymer. The reaction mixture was subjected to a purification treatment in the same manner as in Example 1 to give 105 mg of a fleecy yellow solid. The experimental result was substantially the same as above when the methotrexate derivative of the formula (V) was replaced with that of the formula (VI) (n=12) or acetone as the reaction solvent was replaced with dimethylsulfoxide or N-methylpyrrolidone.

The solubility behavior of the polymeric conjugate and ultraviolet absorption spectrum of an aqueous solution thereof were substantially identical with that obtained in Example 1. The content of methotrexate in the polymeric conjugate was 25% by weight corresponding to the degree of MTX substitution of 14%.

EXAMPLE 7

Figure 2:
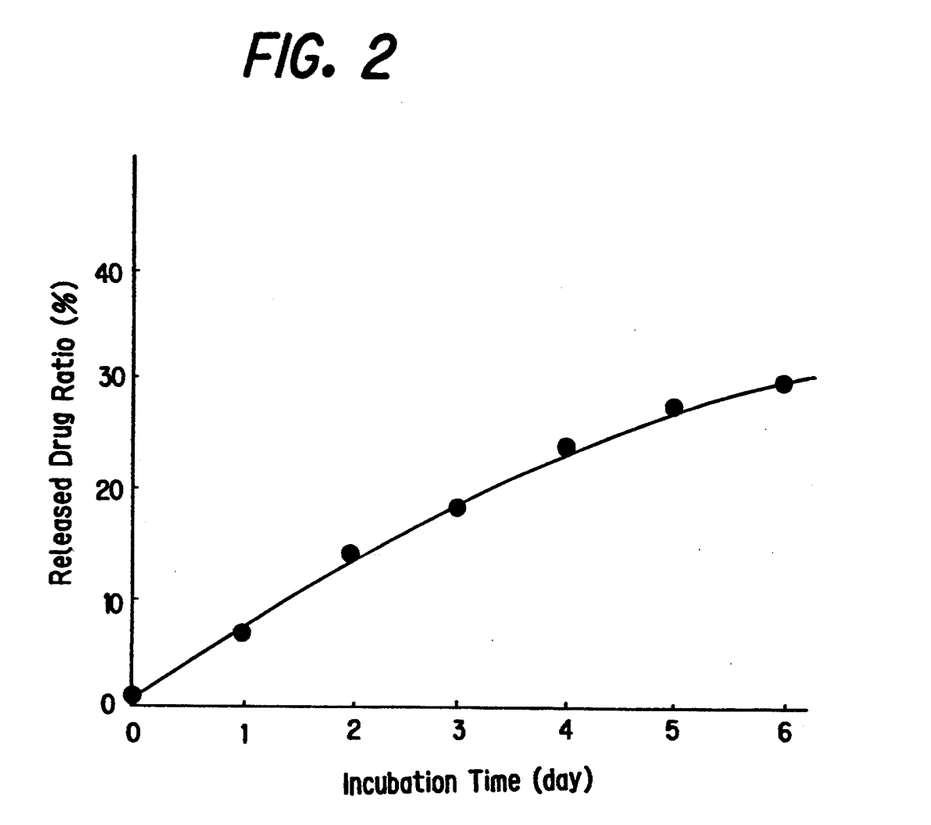
FIG. 2 is a graph showing the release rate of methotrexate from the conjugate determined in the in vitro test using human serum.

The release rate of the methotrexate derivative in serum from the polymeric conjugate thereof was tested in the following manner. Thus, 6.7 mg of the polymeric conjugate prepared in Example 1 were dissolved in 1.0 ml of human serum which was incubated at 37° C. Sampling therefrom was performed to take a 100 µl portion after every 24 hours. The sample serum was admixed with 500 µl of methanol with agitation to precipitate the serum protein which was removed by centrifugation. The liquid phase was subjected to the reversed-phase high performance liquid chromatography using an ODS column for analysis having an inner diameter of 4.6 mm and length of 15 cm using amethopterin as an internal standard to detect the methotrexate derivative. The eluent was a 0.2M ammonium acetate buffer solution of pH 4.6 with a flow rate of 1.0 ml/minute. The eluate was analyzed spectrophotometrically at a detection wavelength of 313 nm. The results are shown in FIG. 2 which indicates the sustained releasability of the methotrexate derivative reaching about 30% release after 6 days.

EXAMPLE 8

The anticancer activity of the polymeric conjugate of methotrexate with pyran copolymer was examined by an animal test. Thus, each of $CD2F_1$ female mice of 6-weeks age was inoculated in the abdominal cavity with $1\times 10^6$ cells of P388 leukemia derived from a $DBA_2$ mouse and, after 24 hours from inoculation of the leukemia cells, administrated once in the abdominal cavity with the test drug in a specified dose by the injection of an aqueous solution thereof. Six a group of the test animals were observed thereafter for the body weight decrease and survival days. Taking the median of the survival days of the mice belonging to the group as the survival day of the group, the life prolongation in % was calculated for each test group relative to the control group. The results are shown in Table 1 below. The administered drug and the administration dose thereof in each of Groups I to V are as follows, in which MTX-hmda is the amidation product of methotrexate and 1,6-diaminohexane prepared in Example 1.

Group I: polymeric conjugate prepared in Example 1, 30 mg/kg
Group II: MTX-hmda, 30 mg/kg, and pyran copolymer, 50 mg/kg, in combination
Group III: methotrexate, 30 mg/kg
Group IV: methotrexate, 150 mg/kg
Group V: pyran copolymer, 50 mg/kg

TABLE 1

| Group | Median survival time (days) | Increase in median survival time (%) |
| --- | --- | --- |
| I | 23.8 | 163.9 |
| II | 16.0 | 77.8 |
| III | 13.9 | 54.4 |
| IV | 15.7 | 74.1 |
| V | 11.0 | 22.2 |
| Control | 9.0 | — |

The results obtained in the above tests for the survival days were subjected to the statistical significance test by the Mann-Whitney U-test to find that the differences between any two groups were significant ($\alpha<0.05$). Namely, the administration of the polymeric conjugate is significantly by far more effective than methotrexate per se alone, the pyran copolymer alone or the combination of the methotrexate derivative and the pyran copolymer.

What is claimed is:
1. A methotrexate conjugate of a pyran copolymer which consists of:
from 10 to 500 in number of the repeating units represented by the general formula in which at least 10% by moles of the groups denoted by R are each a modified methotrexate residue expressed by the formula in which the subscript m is a positive integer in the range from 10 to 500, with a methotrexate compound represented by the general formula or in which the subscript n is a positive integer not exceeding 12, the remainder of the groups denoted by R, if any, being hydroxyl groups, in the form of a free acid or in the form of a salt thereof.

2. A method for the preparation of a methotrexate-pyran copolymer conjugate in the form of a free acid which comprises the step of: reacting, in the presence of a water-soluble organic solvent, a pyran copolymer represented by the general formula in which the subscript n is a positive integer not exceeding 12 in an amount of at least $0.1 \times m$ moles per mole of the pyran copolymer, m having the same meaning as defined above.

3. A therapeutic method against cancer which comprises administrating a patient of cancer with a methotrexate conjugate of a pyran copolymer which consists of: from 10 to 500 in number of the repeating units represented by the general formula in which at least 10% by moles of the groups denoted by R are each a modified methotrexate residue expressed by the formula in which the subscript n is a positive integer not exceeding 12, the remainder of the groups denoted by R, if any, being hydroxyl groups, in the form of a free acid or in the form of a salt thereof.

* * * * *